(12) United States Patent
Bailleul

(10) Patent No.: US 7,931,030 B2
(45) Date of Patent: Apr. 26, 2011

(54) REGIMENS FOR INTRA-ARTICULAR VISCOSUPPLEMENTATION

(75) Inventor: François Bailleul, Paris (FR)

(73) Assignee: Genzyme Corporation, Cambridge, MA (US)

( * ) Notice: Subject to any disclaimer, the term of this patent is extended or adjusted under 35 U.S.C. 154(b) by 759 days.

(21) Appl. No.: 11/313,706

(22) Filed: Dec. 20, 2005

(65) Prior Publication Data

US 2006/0148755 A1 Jul. 6, 2006

Related U.S. Application Data

(60) Provisional application No. 60/640,749, filed on Dec. 30, 2004.

(51) Int. Cl.
| | |
|---|---|
| *A61B 19/00* | (2006.01) |
| *A01N 43/04* | (2006.01) |
| *A61F 2/02* | (2006.01) |
| *A61F 2/08* | (2006.01) |

(52) U.S. Cl. ..... 128/898; 514/54; 623/11.11; 623/14.12; 623/23.72; 623/23.75

(58) Field of Classification Search ............... 623/14.12, 623/23.72, 23.75; 128/898; 514/54
See application file for complete search history.

(56) References Cited

U.S. PATENT DOCUMENTS

| | | | |
|---|---|---|---|
| 4,716,224 A | | 12/1987 | Sakurai |
| 4,801,619 A | * | 1/1989 | Lindblad ........................ 514/42 |
| 4,808,576 A | * | 2/1989 | Schultz et al. ................. 514/54 |
| 5,399,351 A | * | 3/1995 | Leshchiner et al. .......... 424/422 |
| 5,612,321 A | * | 3/1997 | Nguyen .......................... 514/54 |
| 5,690,961 A | * | 11/1997 | Nguyen ........................ 424/488 |
| 6,031,017 A | | 2/2000 | Waki |
| 6,096,728 A | * | 8/2000 | Collins et al. .................... 514/62 |
| 6,527,760 B1 | * | 3/2003 | Vad ................................ 604/512 |
| 6,602,859 B2 | | 8/2003 | Miyamoto |
| 6,630,457 B1 | * | 10/2003 | Aeschlimann et al. .......... 514/54 |
| 6,677,321 B1 | * | 1/2004 | Levin ............................ 514/154 |
| 6,733,753 B2 | * | 5/2004 | Boone et al. ................ 424/134.1 |
| 6,800,298 B1 | * | 10/2004 | Burdick et al. ............... 424/489 |
| 7,119,062 B1 | * | 10/2006 | Alvis et al. ........................ 514/2 |
| 2003/0166706 A1 | * | 9/2003 | Kilgore et al. ................ 514/419 |

(Continued)

FOREIGN PATENT DOCUMENTS

WO  WO 2007/070547 A2  6/2007

OTHER PUBLICATIONS

Hamburger et al. "Intra-Articular Hyaluronans: A Review of Product-Specific Safety Profiles." Seminars in Arthritis and Rheumatism, vol. 32, No. 5 (2003): 296-309.*

Miller et al. "The Value of Intra-Articular Injections in Osteoarthritis of the Knee". The Journal of Bone and Joint Surgery 40B(1958): 636-643.*

(Continued)

*Primary Examiner* — David Isabella
*Assistant Examiner* — Andrew Iwamaye
(74) *Attorney, Agent, or Firm* — B. Timothy Creagan

(57) ABSTRACT

The invention provides viscosupplementation methods for treating osteoarthritis and joint injury with HA-based viscosupplements, particularly viscosupplements with an intra-articular residence half-life shorter than 3 weeks. Viscosupplements for use in the methods of the invention may be further characterized in that they contain less than 20 mg/ml HA, at least 5% (w/w) of which is in a gel form, such as, e.g., hylan B. In an illustrative embodiment, hylan G-F 20 (Synvisc®) is administered in a single intra-articular knee injection of 6±2 ml.

32 Claims, 1 Drawing Sheet

U.S. PATENT DOCUMENTS

| | | | |
|---|---|---|---|
| 2005/0026867 A1* | 2/2005 | Benedict | 514/54 |
| 2005/0080037 A1* | 4/2005 | Petrella | 514/54 |
| 2005/0142152 A1 | 6/2005 | Leschiner | |
| 2006/0040894 A1* | 2/2006 | Hunter et al. | 514/54 |
| 2006/0148755 A1 | 7/2006 | Bailleul | |
| 2007/0036745 A1 | 2/2007 | Leschiner | |
| 2007/0249557 A1* | 10/2007 | Jay | 514/54 |

OTHER PUBLICATIONS

Conrozier Thierry et al.: "Factors predicting long-term efficacy of Hylan GF-20 viscosupplementation in knee osteoarthritis." Joint, Bone, Spine: Revue du Rhumatisme, Mar. 2003, vol. 70, No. 2, Mar. 2003 pp. 128-133.

Lussier, A. et al., "Viscosupplementation with Hylan for the Treatment of Osteoarthritis: Findings from Clinical Practice in Canada" Journal of Rheumatology, Toronto, Canada vol. 23, No. 9, Sep. 1, 1998, pp. 1579-1585.

Anonymous: "Synvisc Hylan G-F 20 patient Information" Internet article Nov. 15, 2004 http: //www.synvisc.com/ussyn_synvisc_pi.pdf.

Altman, R.D. et al., "Efficacy and safety of a single intra-articular injection of non-animal stabilized hyaluronic acid (NASHA) in patients with osteoarthritis of the knee" Osteoarthritis and Cartilage 2004 United Kingdom, vol. 12, No. 8, Aug. 2004 pp. 642-649.

Brandt, K.D. et al., "Intraarticular Injection of Hyaluronan as a Treatment for Knee Osteoarthritis: What is the evidence" Arthritis and Rheumatism, Jun. 2000, vol. 43, No. 6, pp. 1192-1203.

Bellamy N., et al., Vicosupplementation for the Treatment of Osteoarthritis of the Knee, Cochrane Database of Systematic Reviews 2006, Issue 2, Art. No. CD005321. DOI: 10.1002/14651858.CD005321, republished with edits Jan. 21, 2009.

Sinha S., Single vs. Multiple Dose Intra-Articular Hyaluronic Acid in Patients with Osteoarthritis Knee—a Prospective Clinical Trial, Osteoarthritis and Cartilage 2003, 11 Suppl (A): 43.

Scale, Viscosupplementation of Osteoarthritic Knees with Hylan: A Treatment Schedule Study, Current Therapeutic Research, vol. 55, No. 3, Mar. 1994.

Akermark, Non-Animal Stablised Hyaluronic Acid in the Treatment of Osteoarthritis of the Kneee, Clin Drug Invest 2002:22(3) 157-166.

Kolarz, Long-Term Benefits and Repeated Treatment Cycles of Intra-Articular Sodium Hyaluronate (HYalgan) in Patients with Osteoarthritis of the Knee, Seminars in Arthritis and Rheumatism, vol. 32, No. 5 (Apr. 2003, pp. 310-319.

Wobig, Viscosupplementation fith Hylan G-F 20: A 26-Week Controlled Trial of Efficacy and Safety in the Osteoarthritic Knee; Clinical Therapeutics, The International Peer-Reviewed Journal of Drug Therapy, May-Jun. 1998, vol. 20, No. 3.

Genovese, Joint and Soft Tissue Injection, Postgraduate Medicine, vol. 103, No. 3, Feb. 1998.

Heilmann, Das Synovia-Volumen gesunder and arthrotischer menschlicher Kniegelenke, Z. Orthop. 134 (1996).

Carrabba, The Safety and Efficacy of Different Dose Schedules of Hyaluronic Acid and the Treatment of Painful Osteoarthritis of the Knee with Joint Effusion, European Journal of Rheumatiology and Inflammation, vol. 15, Issue 1 1995.

Waddell, An Open-Label Study of a Second Course of Hylan G-F20 for the Treatment of Pain Associated with Knee Osteoarthritis; Current Medical Research and Opinions, vol. 19, No. 6, 499-507.

Intra-articular viscosupplementation for treatment of osteoarthritis of the knee, MSAC application 1045, Assessment Report, Mar. 2003.

Durolane Instructions for Use.

Ryuji, Clinical Trial of SLM-10 (Sodium Hyaluronate Injection) Compared with ARTZ in Patients with Periathritis Scapulohumeralis; Japanese Pharmacology & Therapuetics), 1993, vol. 21 No. 1 (abstract).

Masaya, Clinical Evaluation of SLM-10 (Sodium Hyaluronate Injection) In Patients with Osteoarthritis of the Knee: A Multi-Center Comparative Trial with ARTZ as a Control Drug, Japanese Pharmacol. & Therapeutics), 1993, vol. 21, No. 1, (abstract).

Hisashi, Clinical Effects and Analysis of Synovial Fluid after Intra-Articular Injections of High Molecular Weight Hyaluronate (SLM-10) in Patients with Osteoarthritis of the Knee with the Hydrops, Japanese Pharmacology and Therapeutics, 1993, vol. 21, supp 2, (abstract).

Keiro, A Study of the Effect of Intra-articular Injection of High Molecular Weight Sodium Hyaluronate (SLM-10) on Osteoarthritis of the Knee Joint, Japanese Pharmacol. & Therapeutics), 1993, vol. 21, No. supp2 (abstract).

Fuho, A Study of the Effect High Molecular Weight Sodium Hyaluronate (SLM-10) on Osteoarthritis of the Knee Joint, Japanese Pharmacol & Therapeutics), 1993, vol. 21, No. supp2, (abstract).

Yoichi, A Study of the Effect of SLM-10 on Osteoarthritis of the Knee, Japanese Pharmacol. & Therapeutics), 1993, vol. 21, No. Supp. 2, (abstract).

Shohei, A Study of the Effect of Intra-articular Injection of SLM-10 (Sodium Hyaluronate) on Osteoarthritis of the Knee, Japanese Pharmacology & Therapeutics), 1993, vol. 21, No. supp2 (abstract).

Ryuji, Dose-Range Finding Study of SLM-10 (Sodium Hyaluronate Injection) in Patients with Periarthritis Scapulohumeralis), 1993, vol. 21, No. supp 2, (abstract).

Ken'Ichi, Phase 1 Clinical Study of SLM-10 (High Molecular weight Sodium Hyaluronate Intra-articular Injection) Japanese Pharmacol. & Ther., 1993, vol. 21, No. suppl 2 (abstract).

Keiro, A Study of the Effect of Intra-articular Long Term Injection of High Molecular Weight Sodium Hyaluronate (SLM-10) on Osteoarthritis fo the Knee Joint, Japanese Pharmacol. & Therapeutics) 1993,, vol. 21, No. Supp 2, (abstract).

Shigeaki, Clinical Effect of SLM-10 (High Molecular Weight Sodium Hyaluronate) in Patients with Periatritis of the Shoulder, Japanese Pharmacol. & Therapeu) 1993, vol. 21, No. Supp 2 (abstract).

Keizo, Clinical Evaluation of SLM-10 (High Molecular Weight Sodium Hyaluronate) on Periarthritis of the Shoulder, Japanese Pharm. & Ther) 1993, vol. 21, No. Supp 2, (abstract).

Masaya, Dose-Range Finding Study of SLM-10 (Sodium Hyaluronate Injection) in Patients with Osteoarthritis fo the Knee, Japanese Phar. & Ther.) 1993, vol. 21, No. Supp 2, (abstract).

Masaya, Early Phase II Clinical Study of SLM-10 (Sodium Hyaluuronate) in Patients with Osteoarthritis Knee Joint, Japanese Pharm. & Ther, 1993, vol. 21, No. Supp 2 (abstract).

Anika Therapeutics, "Monovisc-A single Injection. A Singular Treatment," http:monovisc.com/important-facts/index.html, 2 pp.

Health News Daily, Elsevier, Dec. 10, 2008 vol. 20, Issue 239 "FDA Panel Endorses Genzyme's Synvisc-One Knee Therapy".

Hamburger et al, "Intra-Articular hyaluronans: A Review of Product-Specific Safety Profiles", Seminars in Arthritis and rheumatism, vol. 32, No. 5 (Apr. 2003) pp. 296-309.

Genzyme Press Release, Feb. 26, 2009 "FDA approves Genzyme's Synvisc-One Osteoarthritis of the Knee", http://www.genzyme.com/corp/media/Genz%20PR-022609.asp, 2 pages.

Seikagaku Corporation, Press Release (Japanese and English translation) Jul. 18, 2006, Announcement of clinical Study of Cross-linked Hyaluronic Acid Gel To Be Initiated in the US.

Seikagaku Corporation, "gel-200 Versus Placebo in Osteoarthritis of the knee" http://clinicaltrial.gov/show/NTC00449696, 3 pages.

Seikagaku corporation, "Gel-200 Extension and Open-Label Study in Osteoarthritis of the Knee", http://clinicaltrial.gov/ct2/show/NCT00450112, 3 pages.

Anika, News Release Dec. 3, 2008, Anika Therapeutics Completes Enrollment in MONOVISC™ Pivotal U.S. Clinical Trial, http://phx.corporate-ir.net/phoenix.zhtml?c=64664&p=irol-newsArticle&ID=1232170&highlight=.

Genzyme, Biosurgery Intelligence alert Feb. 24, 2009: Cingal CE Mark SUbmission Planned for 2009, 1 pp.

Anika Therapeutic, Inc, "Safety and Effectiveness Study of Hyaluronic Acid in Osteoarthritis" http://clinicaltrial.gov/ct2/show/NCT00653432?term=Monovisc&rank=1, 3 pages.

Anika Therapeutics, "Monovisc", http://www.anikatherapeutics.com/products/jointhealth/monovisc.html, 1 page.

* cited by examiner

REGIMENS FOR INTRA-ARTICULAR VISCOSUPPLEMENTATION

FIELD OF THE INVENTION

This invention relates to rheumatology and orthopaedics. More specifically, the invention relates to treatment of cartilage pathology (e.g., osteoarthritis) by viscosupplementation.

BACKGROUND OF THE INVENTION

Osteoarthritis (OA) is a progressive degenerative disorder characterized by a breakdown of the cartilage in the joints, a deterioration of the synovial fluid present in the articular joints, and a subchondral osteosclerosis accompanied by osteophyte formation. Patients with OA often exhibit severe pain that affects many aspects of their daily living. The prevalence of OA increases with age, with more than 60% of those 60 years old or older likely to have some cartilage abnormality (Bjelle (1982) Scand. J. Rheumatol. Suppl., 43:35-48). OA has become the most costly form of arthritis, collectively accounting for up to 1-2.5% of the gross national product of Western nations (Reginster (2002) Rheumatology, 41 (Suppl. 1):3-6).

Synovial fluid lubricates and protects the intra-articular joint surfaces. The fluid is primarily composed of high molecular weight polysaccharide hyaluronan (HA, sodium salt of hyaluronic acid, also known as sodium hyaluronate). The concentration of HA in the normal human synovial joint fluid is approximately 3 mg/ml. HA consists of repeating disaccharide units of N-acetylglucosamine and sodium glucuronate (FIG. 1). HA in the normal synovial fluid of the joints contains 12,500 disaccharide units with total molecular weight (MW) of 5 MDa (Balazs et al. (1993) J. Rheumatol. Suppl., 39:3-9). In OA patients, the concentration and MW of HA in synovial fluid decreases, resulting in the diminished capacity of the fluid to protect the cartilage.

Intra-articular injection of an elastoviscous solution containing high molecular weight HA has been shown to restore the normal homeostasis of the diseased joint. This procedure, known as viscosupplementation, has proven effective in reducing pain and enhancing joint function (see, e.g., Balazs et al. (1993) J. Rheumatol. Suppl., 39:3-9; Wobig (1998) Clin. Ther., 20(3):410-423).

A number of HA-based viscosupplements are available on the market and new products are being developed. Viscosupplements vary in a number of characteristics including, for example, the source of HA (animal-derived or bacterial), the concentration and MW of HA, and the type and degree of chemical crosslinking used, if any. Usually, most viscosupplements contain 5-15 mg/ml HA and, once injected, have residence half-life between hours to several days. Such viscosupplements are injected into the knee in 2-3 ml unit volumes in a series of three to five injections each one week apart. In some cases, pain relief occurs within a few days, continues to progress over a few weeks, and often lasts for several months, even up to a year. For example, knee viscosupplementation with Synvisc® (hylan G-F 20; Genzyme Corp., Cambridge, Mass.) administered three times at 2 ml weekly has been demonstrated to be at least as good, or better, than continuous oral therapy with non-steroidal anti-inflammatory drugs (NSAIDs) plus arthrocentesis over a period of 6 months (Adams et al. (1995) Osteoarthritis and Cartilage, 3:213-225) and more effective than a saline placebo or arthrocentesis controls (Moreland (1993) Am. Coll. Rheumatol. (57th Ann. Sci. Meeting, Nov. 7-11, San Antonio, Tex.), 165; Wobig (1998) Clin. Ther., 20(3):410-423).

The series of multiple injections have been thought to be essential for a prolonged (six months to one year) effect on osteoarthritic pain primarily because of the short residence half-life of most viscosupplements (Peyron (1993) J. Rheumatol., 20(Suppl. 39):10-15). For example, an intra-articular residence half-life of 1% HA with an average MW of 1.7-2.6 MDa is 11 hours, as determined in rabbits. As MW of HA increases, so does the residence half-life (e.g., 1% hylan A, in which the average MW of HA is 6 MDa, has a half-life of 1.2±1 day). However, even an insoluble gel, such as hylan B containing 0.4% HA, has a relatively short residence half-life of 7.7±1 days. Consistent with the half-life data, three 2 ml injections of Synvisc® (hylan G-F 20) into an OA knee were demonstrated to be significantly more effective for reducing OA pain than two 2 ml injections (Scale et al. (1994) Curr. Ther. Res., 55(3):220-232).

For treatment with Synvisc® of patients with OA of the hip, the recommended dose is one 2 ml injection with a second optional injection administered between one and three months if insufficient pain relief is experienced (Chevalier (2000) Am. Coll. Rheumatol. (64th Annual Scientific Meeting, Oct. 30-Nov. 3, Philadelphia, Pa.)). In hip OA patients, a single intra-articular injection of Synvisc® (hylan G-F 20) at 2 ml showed a significant immediate and sustained symptomatic effect in the majority of enrolled patients for up to three months (duration of the study). It has not been investigated whether greater volumes of viscosupplements, such as Synvisc® (hylan G-F 20) (e.g., 4, 6 ml or greater), could offer equivalent or better efficacy with fewer injections compared to multiple injection of 2-3 ml, or a single injection of 2 ml. As far as was known, the use of larger volumes potentially posed a risk of local adverse effects such as pain, swelling, and effusion.

Durolane™ (Q-Med AB, Uppsala, Sweden) is the only viscosupplement that is recommended to be injected once, at 3 ml. It is an epoxy-crosslinked viscosupplement with a longer reported half-life (4 weeks) and a higher concentration of HA (20 mg/ml). The prolonged residence time is thought to allow the reduced number of injections. Nevertheless, a single injection of Durolane™ did not demonstrate statistical benefits over placebo (Altman et al. (2004) Osteoarthritis and Cart., 12:642-649).

Thus, prior to the present invention, it was not known whether a single injection of an HA-based viscosupplement, particularly one with a short residence life, can produce a desired long-term therapeutic effect.

The use of fewer injections offers apparent advantages over the multiple injections, including avoidance of adverse effects, reduced costs, and better patient compliance. A continued need exists to develop new viscosupplementation treatments that provide effective relief to OA patients without necessitating multiple injections.

SUMMARY OF THE INVENTION

The invention provides methods and compositions for treating joint pathology, and for reducing pain and discomfort associated with such pathology. Examples of such pathology include osteoarthritis and joint injury.

The invention is based, at least in part, on the discovery that a single intra-articular injection of a greater volume of a viscosupplement provides long-term therapeutic benefits comparable to those produced by serial injections of smaller volumes. In a study conducted in connection with the invention, one group of knee OA patients received the standard sequence of three 2 ml injections of Synvisc® (hylan G-F 20) in the knee over a three-week period, while another group received a single injection of 6 ml under identical conditions. Surprisingly, therapeutic efficacy, as evaluated at 26 weeks following the treatment, was found to be comparable in both groups. Thus, a single injection of a greater volume of a viscosupplement, such as Synvisc® (hylan G-F 20), can be as effective as several injections of smaller volumes, while maintaining a favorable safety profile.

Accordingly, the invention provides regimens for intra-articular viscosupplementation with HA-based viscosupplements, particularly viscosupplements with intra-articular residence half-life ($T_{1/2}$) shorter than 3 weeks. Viscosupplements for use in the methods of the invention may be further characterized in that they contain less than 20 mg/ml HA (derivatized and/or nonderivatized), at least 5% of which is in a gel form such as, e.g., hylan B. In an illustrative embodiment, the viscosupplement is hylan G-F 20 (Synvisc®), which contains 8±2 mg/ml HA, of which 10% by weight is in a gel form.

In some embodiments, a viscosupplement is administered in a single injection in an amount sufficient to provide a therapeutic effect for up to 6 months following the injection. In some embodiments, the therapeutic effect of a single injection of a larger volume is substantially the same as that achieved by three injections (each ⅓ of the larger volume) administered over a course of treatment. In an illustrative embodiment, Synvisc® (hylan G-F 20) is administered in a single injection of 6 ml, rather than three 2 ml injections, over a three-week period.

Methods of administration, compositions and devices used in the methods of the invention are also provided.

The foregoing summary and the following description are not restrictive of the invention as claimed.

DETAILED DESCRIPTION OF THE INVENTION

Definitions

Figure 1:
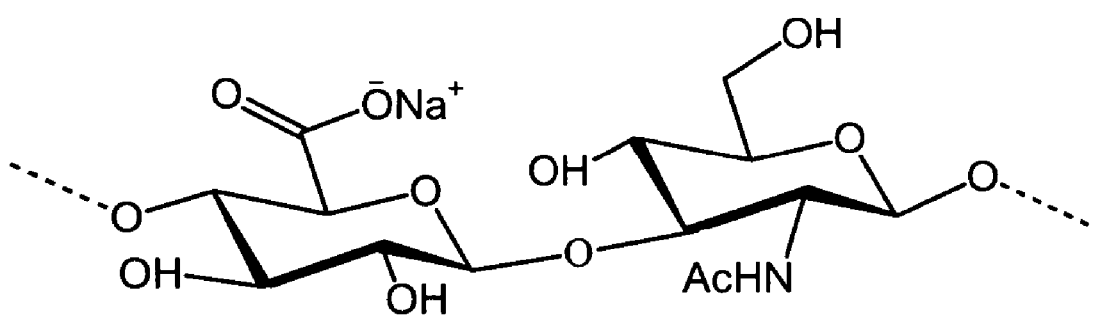
FIG. 1 illustrates the structure of hyaluronan (sodium hyaluronate).

The terms "intra-articular half-life," "residence half-life," and their cognates refer to the time which is the greater of any of the times applicable to a given viscosupplement injected into the intra-articular space: (a) the time required for clearance of 50% of the HA gel component injected; (b) the time required for clearance of 50% of the HA fluid component injected; and (c) the time required for clearance of 50% of HA, regardless whether it is fluid, gel, or another form. For the purposes of residence half-life calculation, unless stated otherwise, the injection is considered to be administered into the intra-articular space of a knee joint of an adult human. Methods for determining residence half-life are known in the art and illustrative methods are described in the Examples.

The terms "HA fluid," "HA fluid phase," "HA fluid component," "soluble HA," and their cognates refer to uncrosslinked or lightly crosslinked water-soluble HA with an average MW of less than 20 MDa.

The term "HA gel," "HA gel phase," "HA gel component," and their cognates refer to HA gel which is a water-insoluble part of an HA-based composition that does not contain soluble HA or contains less than 10% (w/w) of soluble HA. Typically, the amount of gel in a given HA-based composition containing a mix of HA gel and HA fluid can be determined by separating HA gel from HA fluid. The separation can be accomplished by filtering the composition through, e.g., a 45μ filter, which passes through soluble HA yet retains the insoluble phase. In order to maximize the release of soluble HA from the HA gel in more viscous compositions, a composition may need to be diluted with several volume of a solvent with or without bringing it to the equilibrium prior to filtration. Furthermore, generally, pure gels can be distinguished from pure fluids based on their rheological properties, such as storage (elastic) modulus (G') and loss (viscous) modulus (G"), which represent respectively the relative degrees a material can recover (elastic response) or flow (viscous response) as the rate of deformation (test frequency) changes. Both moduli are linear functions of the frequency. They have proven to be sensitive probes of the structure of polymer solutions and gels. Both G' and G" increase with increasing frequency, but one increases more quickly than the other. At the point where G'=G", this frequency is called cross-over frequency ($f_c$). The cross-over frequency decreases with increasing polymer molecular weight or concentration. For a polymer solution at low frequency, elastic stresses relax and viscous stresses dominate, and as a result G" is greater than G' at frequencies below $f_c$. In contrast, for a gel, there is no cross-over between G' and G", and G' is greater than G" across the frequency range. Unless otherwise specified, the test frequency is 0.04-7 Hz. For a review of physical properties of viscoelastic materials and methods of measuring these properties, see, e.g., "Polymers as Rheology Modifiers", edited by Schulz and Glass, ACS Symposium Series 462, 1991; "An Introduction to Rheology," H. A. Barnes, J. F. Hutton and K. Walters, Elsevier, 1989; and Bohlin Rheometer Application Notes MRK544-01, MRK556-01, and MRK573-01.

The terms "HA," "hyaluronate," "hyaluronan" are used interchangeably, and unless stated otherwise, refer to any HA, regardless of the source (bacterially fermented or animal-derived), molecular weight, its physical form (e.g., gel or fluid), or the presence or absence of chemical modifications (e.g., crosslinked or otherwise derivatized), or method of production.

Regimens

The invention provides viscosupplementation methods and related methods. According to the invention, viscosupplementation methods consist of administering a single intra-articular injection of viscosupplement within a period of 3, 4, 5, 6, 7, 8, 9, 10, 11, 12, 13, 14, 15, 16, 17, 18, 19, 20, 21, 22, 23, 24, 25, 26 weeks, in the amount sufficient to provide a therapeutic effect for up to 4, 5, or 6 months following the injection. In some embodiments, the therapeutic effect of a single injection of a larger volume is substantially the same as that achieved by three injections (each ⅓ of the larger volume) administered over a course of treatment. In some embodiments, the single injection regimen provides reduced joint pain for up to 4, 5, or 6 months following the injection.

The therapeutic effect can be assessed by any suitable method (see, e.g., Altman et al. (1996) Osteoarth. Cart., 4:217-243). For example, the therapeutic effect may be assessed by measuring a reduction in joint pain. The degree of joint pain can be classified according to a five-point Likert scale (e.g., none, mild, moderate, severe, very severe) or on a 100 mm visual analog scale (VAS) as described in the Examples. Other suitable pain indices include the Health Assessment Questionnaire (HAQ) (Fries et al. (1980) Arthritis Rheumatol., 23:137-145) and Arthritis Impact Measurement Scale (AIMS) (Meenan et al. (1980) Arthritis Rheumatol., 23:146-154.

The therapeutic effect may also be assessed by measuring the improvement in the degree of functional impairment. Functional impairment can be measured by using a segregated, validated multidimensional index (SMI) such as the Western Ontario and McMaster's Universities (WOMAC™) OA index for hip and knee OA (Bellamy et al. (1988) J. Rheumatol. 34:1833-1840; see, also, Examples); or an aggregated multidimensional index (AMI) such as the Algo-Functional Index (AFI) for hip or knee (Lequesne et al. (1987) Scand. J. Rheumatol. Suppl., 65:85-89).

The therapeutic effect may also be evaluated by global status assessment by a patient or a physician. Global status can be assessed using a Likert or VAS scale, e.g., as described in the Examples.

Additional indicia of therapeutic effect may include joint examination (see, e.g., Theiler et al. (1994) Osteoarth. Cart., 2:1-24), performance based measures (see, e.g., Rejeski et al. (1995) Osteoarth. Cart., 3:157-168), etc.

In some embodiments, a viscosupplement is administered into the knee joint in the amount of 6±2 ml or more, e.g., 4, 4.25, 4.5, 4.75, 5, 5.25, 5.5, 5.75, 6, 6.25, 6.5, 6.75, 7, 7.25, 7.5, 7.75, 8 ml or more.

Viscosupplements

An HA-based viscosupplement useful in the methods of the invention is characterized by any one, any two, or all of the features as follows:
 (i) the viscosupplement has a residence half-life of less than 3 weeks;
 (ii) the viscosupplement contains less than 20 mg/ml HA;
 (iii) 5% (w/w) or more of HA in the viscosupplement is in a gel form.

In an illustrative embodiment, the viscosupplement used in the methods of the invention is Synvisc® (hylan G-F 20). Synvisc® (hylan G-F 20) contains 8±2 mg/ml HA in two forms: a soluble form, hylan A, (average MW 6,000 kDa) and a hydrated gel form, hylan B, in a physiologically acceptable solution. The hylan A/hylan B ratio in Synvisc® (hylan G-F 20) is 9:1 by weight of HA. Hylan A is a water-soluble hyaluronan chemically modified by covalent crosslinking with small amounts of an aldehyde, typically formaldehyde, while hylan B is hylan A further crosslinked by divinyl sulfone. Hylan fluid is hydrated hylan A, a modified form of hyaluronan with a small number of crosslinks which increase its average molecular weight and augment its elastoviscous properties. Hylan gel is the hydrated form of hylan B, and is prepared by crosslinking hylan A into a continuous polymeric network, using divinyl sulfone as a bifunctional crosslinking reagent.

Generally, viscosupplements used in the regimens provided by the invention include HA-based viscosupplements having intra-articular residence half-life shorter than 22 days, e.g., 21, 20, 19, 18, 17, 16, 15, 14, 13, 12, 11, 10, 9, 8, 7, 6, 5, 4, and 3 days. In some embodiments, residence half-life of the viscosupplement is more than 2, 3, 4, 5, 6, or 7 days.

Viscosupplements used in the methods of the invention may be further characterized in that they contain less than 20 mg/ml HA, e.g., in the range of 1-15, 1-10, 1-5, 5-15, 5-10, 10-15, 6-10, and 7-9 mg/ml. The amount of HA in a given composition can be determined by any suitable methods as described, e.g., in the Examples.

Viscosupplement compositions used in the methods of the invention may be further characterized in that at least 10% by weight of HA in the viscosupplement is in a gel form. For example, in some embodiments, the viscosupplement comprises at least 5%, 10%, 15%, 20%, 25%, 30%, 35%, 40%, 50%, 55%, 60%, 65%, 70%, 75%, 80%, 85%, 90%, 95%, 99% or more HA gel. In some embodiments, the viscosupplement contains 10-90%, 10-75%, 10-50%, 10-40%, 10-25% HA gel. In some embodiments, the ratio of HA gel/HA fluid in the viscosupplement contains ranges from 1:50-10:1 (w/w), e.g., 1:50, 1:25, 1:15, 1:10, 1:9, 1:8, 1:7, 1:6, 1:5, 1:4, 1:3, 1:2; 1:1, 2:1, 3:1, 4:1, 5:1, 6:1, 7:1, 8:1, 9:1, and 10:1.

Viscosupplements for use in the methods of the invention may further contain water-soluble HA in a fluid phase, with MW of HA in the range of 500-20,000 kDa, e.g., 500-1,000, 500-1,500; 500-3,000; 500-5,000; 500-7,000; 500-10,000; 500-15,000; 1,000-1,500; 1,000-3,000; 1,000-5,000; 1,000-7,000; 1,000-10,000; 1,000-15,000; 5,000-10,000; and 10,000-15,000 kDa.

HA may be of animal origin, e.g., derived from rooster combs or umbilical cords, or non-animal origin, e.g., bacterially fermented. Bacterially fermented HA can be produced as described in, e.g., Cooney et al. (1999) Biotechnol. Prog., 15:898-910. Bacterially fermented HA is also available commercially (e.g., Shiseido, Japan; Sigma-Aldrich, USA).

HA may be derivatized (e.g., crosslinked or otherwise modified or stabilized) or nonderivatized. Examples of crosslinkers include aldehyde, epoxide, polyaziril, glycidyl ether (e.g., 1,4-butandiol diglycidylether), and divinyl sulfone.

Specific examples of viscosupplements useful in the methods of inventions include Adant™, Arthrease™, Arthrum™, Fermathron™, Go-on™, Hyalart™/Hyalgan™, Hy-GAG™, Hya-ject™, Hyalubrix™, NeoVisc™, Supartz™/Artz™, Synvisc® (hylan G-F 20), Orthovisc™, Ostenil™, Sinovial™, Suplasyn™, and Synochrom™, Viscorneal™ (see, e.g., Physicians' Desk Reference™, 2004). Other products suitable in the methods of the invention include viscosupplements described in U.S. Pat. Nos. 5,143,724; 4,713,448; 5,099,013; 5,399,351; 6,521,223; 5,827,937; U.S. Patent Application No. 60/533,429.

Preparation of hylans and viscosupplements including linoleum hylan A and hylan B is described in, e.g., U.S. Pat. Nos. 5,143,724; 4,713,448; 5,099,013; and 5,399,351.

In some embodiments, the viscosupplements exclude Durolane™ and/or other viscosupplements with a residence half-life of longer than 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 days.

Viscosupplements may also contain additional active or inactive components including, for example, the non-steroidal anti-inflammatory drugs (NSAIDs), e.g., Ibuprofen™, Diclofenac™, and Piroxicam™; anaesthetics, e.g., Lidocaine™ and Bupivacaine™; opioid analgesics, e.g., codeine and morphine; corticosteroids, e.g., dexamethasone and prednisone; antineoplastic agents such a Methotrexate™, 5-fluorouracil and Paclitaxel™; and anti-viral agents, e.g., Acyclovir™ and Vidarabine™. Viscosupplements may also contain components such as cells (e.g., chondrocytes or mesenchimal stem cells), proteins, DNA, vitamins or other desirable biologically active material.

Uses and Administration

The invention provides methods and composition for treating subjects with joint pathology and for reducing pain and discomfort associated with such pathology. Examples of such pathology include osteoarthritis (primary (idiopathic) or secondary), rheumatoid arthritis, joint injury (e.g., repetitive motion injury), cartilage pathology (chondromalacia), and pre-arthritic states. The invention further provides methods of reducing pain associated with such pathologies. The methods can be practiced in humans in need of treatment for joint pathology or in nonhuman subjects.

Examples of administration sites include the knee, shoulder, temporo-mandibular and carpo-metacarpal joints, elbow, hip, wrist, ankle, and lumbar zygapophysial (facet) joints in the spine. The volumes injected into any of these joints would be at least double of the currently recommended dose for that joint.

The invention further provides a viscosupplementation device comprising a pre-filled, single-use syringe having a single unit dosage of 6±2 ml Synvisc® (hylan G-F 20), e.g., 4, 4.25, 4.5, 4.75, 5, 5.25, 5.5, 5.75, 6, 6.25, 6.5, 6.75, 7, 7.25, 7.5, 7.75, 8, 8.25, 8.5, 8.75, 9, 9.25, 9.5, 9.75, 10 ml or more. Although it is preferred to provide the single administration dose with a use of a single syringe provided here, the required dose may be provided with two or more syringes. For example, a single administration of 6 ml may be accomplished using 3 syringes containing 2 ml each.

The following Examples provide illustrative embodiments. The Examples do not in any way limit the invention. One of ordinary skill in the art will recognize numerous modifications and variations that may be performed within the scope of the present invention. Such modifications and variations are therefore encompassed by the invention.

EXAMPLES

Example 1

Intra-Articular Injection of Synvisc® (hylan G-F 20) in Patients with OA

A prospective, open-label study was conducted to evaluate the safety and efficacy (including duration of action) of intra-articular injections of 4 ml or 6 ml of Synvisc® (hylan G-F 20) against the current dosing regimen of three intra-articular injections of 2 ml Synvisc® (hylan G-F 20) in ambulatory patients with symptomatic tibio-femoral OA (global OA pain in the study knee in the range of 50-80 on a 100 mm VAS score). Other criteria for inclusion were: age of 40 years or older; Kellgren-Lawrence grade II-III by X-ray within 3 last months; absence of tense effusion, mechanical deficit, or recent (<2 years) trauma. 100 patients (mean age 61 years ranging from 59 to 66, 55% females) were randomized in five groups:

Group 1—one injection of 6 ml;
Group 2—one injection of 4 ml;
Group 3—two injections of 4 ml two weeks apart;
Group 4—three 4 ml injections one week apart; and
Group 5—the standard regimen of three 2 ml injections one week apart.

The patients were then followed up to 6 months (at weeks 2, 3, 8, 16, and 24). The primary and secondary assessment endpoints used are described below.

A. Patient Self-assessment of OA Pain

The primary efficacy endpoint of this study is to evaluate the efficacy of visco-supplementation with Synvisc® (hylan G-F 20) in patients with OA of the knee with respect to study knee OA pain relief. This is measured on a patient self assessed 100-mm VAS, with endpoints of no pain (0 mm) to extreme pain (100 mm) within the past 48 hours; performed at 24 weeks following the first injection.

B. Patient Global Self-Assessment

The patient rated the overall status of their target knee on the 100-mm VAS which ranged from very good (0 mm) to very poor (100 mm), taking into account all related signs and symptoms over the previous 48 hours. The exact instructions presented to the patient were the following: "Please indicate by using a vertical line below, the overall general condition of your (study) knee at the time of this visit. The left or '0' score indicates 'Very good' while the '100' score indicates 'Very poor'."

C. WOMACT™

The patient completed the VAS version of the WOMAC™ as described in Bellamy et al. (1988) J. Rheumatol., 15(12): 1833-40. This scale is a tri-dimensional, disease-specific, self-administered, health status measure. It probes clinically important, patient-relevant symptoms in the areas of pain, stiffness and physical function in a total of 24 questions. The WOMAC™ was provided to the patient in the local language and was usually completed in less than 5 minutes. The WOMAC™ sub-sections are the following.

The WOMAC™ Section A consists of questions regarding levels of pain during activity and the responses are scored (by the patient) with a VAS that ranges from no pain (0 mm) to extreme pain (100 mm). Assessment of pain is made for the following scenarios:

| | | |
|---|---|---|
| 1. | Walking on a flat surface? | [walking] |
| 2. | Going up or down stairs? | [stair climbing] |
| 3. | At night while lying in bed? | [nocturnal] |
| 4. | Sitting or lying? | [rest] |
| 5. | Standing upright? | [weight bearing] |

The mean sub-score for the WOMAC Section A was based on the responses to each of the components of Section A.

The WOMAC™ Part B (Stiffness Score) consists of questions regarding stiffness severity during activity and the responses are scored (by the patient) with a VAS that ranges from no stiffness (0 mm) to extreme stiffness (100 mm). Assessment of stiffness was made for the following scenarios:

| | | |
|---|---|---|
| 1. | After waking in the morning? | [morning stiffness] |
| 2. | During rest later in the day? | [stiffness occurring later in the day] |

The mean sub-score for Section B was based on the responses to each of the components of Section B.

The WOMAC™ Section C consists of questions regarding functional impairment during activity and the responses are scored (by the patient) with a VAS that ranges from no difficulty (Q mm) to extreme difficulty (100 mm). Assessment of functional impairment was made for the following scenarios:

| | | |
|---|---|---|
| 1. | Descending stairs? | [morning stiffness] |
| 2. | Ascending stairs? | [stiffness occurring later in the day] |
| 3. | Rising from sitting? | [rising sitting] |
| 4. | Standing? | [standing] |
| 5. | Bending to the floor? | [bending] |
| 6. | Walking on flat surfaces? | [flat walking] |
| 7. | Getting in and out of car? | [car] |
| 8. | Going shopping? | [shopping] |
| 9. | Putting on socks/stockings | [socks/stockings off] |
| 10. | Lying in bed | [lying in bed] |
| 11. | Getting in/out of bath | [in/out bath] |
| 12. | Sitting | [sitting] |
| 13. | Getting on/off toilet | [on/off toilet] |
| 14. | Heavy domestic duties | [heavy domestic] |
| 15. | Light domestic duties | [light domestic] |

The mean sub-score for Section C was based on the responses to each of the components of Section C.

The change from baseline in the total WOMAC™ score derived from the 3 WOMAC™ sections (A, B and C) at all time points following the first injection was analyzed as a secondary endpoint.

D. Physician OA Global Assessment

After the patient has completed the global assessments and the WOMAC™, the Investigator rated the overall condition of the patient's knee at the time of the visit on the 100-mm VAS ranging from very good (0 mm) to very poor (100 mm). This evaluation was based on the patient's signs of disease, functional capacity and physical examination. The physician was instructed to indicate the overall general condition of the patient's knee at the time of this visit, using a line presented with the left ("0") extreme of the line indicating "very good" and the right extreme ("100") indicating "very poor."

E. Results

The results showing reduction of pain (VAS; 0 corresponding to no pain and 100 to extreme pain, within the past 48 hours) at 24 weeks following the first injection as compared to baseline is shown in Table 1. Pain dropped by 34.9 mm in the 1×6 ml group as compared with 36.7 mm in the 3×2 ml group which scored the best. In the groups treated by 1×4 or 2×4 ml, this decrease was less dramatic (only 24 mm reduction).

TABLE 1

Patient self-assessment of OA pain (change from baseline)

| | Group | | | | |
|---|---|---|---|---|---|
| | 1<br>1 × 6 ml | 2<br>1 × 4 ml | 3<br>2 × 4 ml | 4<br>3 × 4 ml | 5<br>3 × 2 ml |
| Mean | −34.9 | −24.3 | −24.0 | −32.6 | −36.7 |
| Std. Dev. | 16.4 | 28.3 | 22.9 | 25.3 | 26.9 |
| 95% CI | −42.5,<br>−27.2 | −37.2,<br>−11.5 | −35.0,<br>−13.0 | −44.4,<br>−20.8 | −49.2,<br>−24.1 |

Secondary efficacy endpoints including improvement in pain, stiffness and functional impairment as measured by the Western Ontario and McMaster Universities Osteoarthritis Index (WOMAC™) (Table 2 for WOMAC™ A), patient (Table 3) and physician (Table 4) global knee OA assessments, showed the same trends. Treatment groups were ranked in order of efficacy and the results are shown in Table 5. The prolonged duration of the effect observed in group 1 was surprising. In terms of safety, 10% of the patients in each group (1×6 ml and 3×2 ml) reported related local knee adverse events (pain, swelling or effusion) of minimal or moderate intensity.

TABLE 2

WOMAC ™ A pain score (change from baseline)

| | Group | | | | |
|---|---|---|---|---|---|
| | 1<br>1 × 6 ml | 2<br>1 × 4 ml | 3<br>2 × 4 ml | 4<br>3 × 4 ml | 5<br>3 × 2 ml |
| Mean | −25.8 | −14.7 | −16.6 | −27.7 | −25.6 |
| Std. Dev. | 22.5 | 24.2 | 24.8 | 27.2 | 24.6 |
| 95% CI | −36.3,<br>−15.3 | −25.7,<br>−3.7 | −28.5,<br>−4.6 | −40.5,<br>−14.9 | −37.1,<br>−14.1 |

TABLE 3

Patient global assessment (change from baseline)

| | Group | | | | |
|---|---|---|---|---|---|
| | 1<br>1 × 6 ml | 2<br>1 × 4 ml | 3<br>2 × 4 ml | 4<br>3 × 4 ml | 5<br>3 × 2 ml |
| Mean | −31.3 | −14.3 | −19.8 | −25.9 | −24.4 |
| Std. Dev. | 26 | 31 | 24 | 32.9 | 32.3 |
| 95% CI | −43.4,<br>−19.1 | −28.4,<br>−0.2 | −31.2,<br>−8.2 | −41.3,<br>−10.5 | −39.5,<br>−9.3 |

TABLE 4

Physician global assessment (change from baseline)

| | Group | | | | |
|---|---|---|---|---|---|
| | 1<br>1 × 6 ml | 2<br>1 × 4 ml | 3<br>2 × 4 ml | 4<br>3 × 4 ml | 5<br>3 × 2 ml |
| Mean | −30.7 | −16.8 | −22.9 | −25.9 | −27.7 |
| Std. Dev. | 18.3 | 24.8 | 26.9 | 25.0 | 29.6 |
| 95% CI | −39.5,<br>−21.9 | −28.1,<br>−5.5 | −35.8,<br>−10.0 | −37.5,<br>−14.2 | −41.6,<br>−13.8 |

TABLE 5

Treatment group rankings

| | Group | | | | |
|---|---|---|---|---|---|
| | 1<br>1 × 6 ml | 2<br>1 × 4 ml | 3<br>2 × 4 ml | 4<br>3 × 4 ml | 5<br>3 × 2 ml |
| Pt. pain | 2 | 4 | 5 | 3 | 1 |
| Pt. global | 1 | 5 | 4 | 2 | 3 |
| Phy. global | 1 | 5 | 4 | 3 | 2 |
| WOMAC ™ A | 2 | 5 | 4 | 1 | 3 |
| WOMAC ™ B | 4 | 5 | 3 | 2 | 1 |
| WOMAC ™ C | 2 | 4 | 5 | 1 | 3 |

No large differences were observed between the treatment groups with respect to safety, only that Group 1 (1×6 ml) had in general the least adverse effects. These results also suggest that volumes of Synvisc® (hylan G-F 20) larger than 2 ml can be safely administered to reduce pain in patients with osteoarthritis of the knee.

Example 2

Determination of Synvisc® Residence Half-Life

A. Incorporation of $^{14}$C-Acetate into the Hyaluronan of Rooster Comb Organ Cultures Young roosters (3-6 months of age) were sacrificed by cervical dislocation. Their combs were thoroughly cleansed with (80%) ethanol, and then excised at the base using a scalpel. Excess blood was pressed out of the comb, and it was placed into sterile saline solution, transferred to a laminar flow hood, and rinsed in three additional volumes of sterile saline solution. The comb was then dissected along the vascular midline, and rectangular segments of pink dermal tissue were excised. The comb tissue segments were thinly sliced with a scalpel and placed into Ventrex media HL-1 (Ventrex Labs), 5 mg/ml testosterone propionate (Belmar Laboratories, Inwood, N.Y.), 20 µCi/ml of $^{14}$C-acetic acid (ICN Radiochemicals, Irvine, Calif., 1 mCi/ml), 0.1 mg/ml penicillin, 0.1 mg/ml streptomycin and 0.1 mg/ml fungizone (Hazelton, Lenexa, Kans.). Individual cultures were done in 60 mm plastic Petri dishes and contained approximately 1.5 g of comb tissue and 15 ml of the media. The cultures were incubated for 72 hours in a 5% $CO_2$ environment, after which the tissue was separated from the media by centrifugation for 10 minutes at 10,000 g. The tissue pellet was frozen in a 30 mm Petri dish. The frozen radiolabeled comb tissue was typically kept in the freezer for 1-72 hours prior to continued processing to prepare hylan.

B. Preparation of Radiolabeled Hylan Fluid

Hylan A fibers were prepared as follows. Slices of frozen radiolabeled comb tissue were placed into a reaction medium containing acetone, formalin (37% formaldehyde solution), chloroform, and sodium acetate at a ratio of 0.75 g tissue per 1 g of reaction medium. The reaction was allowed to proceed for 18-20 hours, after which the tissue slices were harvested, washed three times in acetone, and then dried in a laminar flow hood. Four volumes of distilled water were then added to the dry tissue slices in order to extract radiolabeled hylan. This aqueous extraction was performed at 4-6° C., after which the aqueous extract was removed, and an identical volume of water was added back for a second extraction. Solid sodium acetate was dissolved into the aqueous extracts to a concentration of 1%, and hylan fibers were precipitated by the slow addition into four volumes of 95% ethanol. The radiolabeled hylan fibers were washed twice in acetone, and stored in the cold under acetone.

Radiolabeled hylan A fibers (40.3 mg) were pooled and dissolved into 3.0 ml of sterile, pyrogen-free, phosphate buffered saline solution (Biotrics Inc., Ridgefield, N.J., lot 122-1) by slow end-over-end mixing for 3 days at 4° C. After complete dissolution, the radioactive hylan fluid was diluted fivefold with non-labeled hylan fluid. The mixture was kept for an additional five days on the end-over-end mixture at 4° C.

C. Preparation of Radiolabeled Gel

Tritiated water (New England Nuclear, 100 mCi/ml) was mixed into the reaction mixture used to crosslink hylan fluid (hylan A) into hylan gel (hylan B). The crosslinking reaction was run as follows. Hylan A fibers were allowed to swell in the tritiated water for approximately three hours. Concentrated sodium hydroxide was added and the mixture was vigorously stirred until the solution was homogeneous (approximately 15 minutes). Divinyl sulfone was diluted to a concentration of 50% in water, and added into the reaction mixture with vigorous stirring. The reaction mixture was allowed to stand at room temperature (22° C.) for an additional 55 minutes during which the polysaccharide chains were crosslinked by divinyl sulfone into a continuous polymeric gel (hylan gel). By performing this reaction in tritiated water, tritium becomes covalently attached to carbon within the divinyl sulfonyl crosslink. The reaction was terminated by the addition of ten volumes of sterile pyrogen-free saline solution to lower the pH below 12. Saline washing also results in a swelling of the hylan gel to its equilibrium hydration. The hylan gel was washed with saline to remove unreacted divinyl sulfone, unreacted tritium, and other reaction products, and to bring the pH down to 7. Excess saline was separated from the gel by filtration, after which the gel was passed through a 25 g needle 5 times to break up the solid gel into an easily injectable form. In this form, the tritiated gel was exhaustively dialyzed against sterile, pyrogen-free saline to remove any non-covalently bound tritium.

D. Preparation of a Hylan Gel-Hylan Fluid Mixture

Tritiated hylan gel (3.04 g) was directly added into 11.63 g of $^{14}C$-hylan fluid, and the mixture was placed on a Glen Mills mixer for 48 hours. The mixture was then passed ten times through 18 g, 21 g, and 25 g needles successively to assure homogeneity and ease of injection.

E. Measurements of HA Concentration and Radiolabel Amounts

The concentration of hylan polysaccharide in the gel and fluid components of the mixture were determined by the automated carbazole procedure for assaying its repeating glucuronic acid monomer (3) and multiplying by (2.07) to account for the remainder of the polysaccharide chain. Hylan gel was hydrolyzed prior to glucuronic acid determination by adding weighed 0.1 g samples of the gel to 0.2 ml of 1N $H_2SO_4$ in tightly capped screw top tubes, and allowing acid hydrolysis to proceed for 2 hours at 100° C. The samples, which were completely solubilized by this procedure, were neutralized with 0.2 ml of 1N NaOH prior to analyzing HA by a carbazole procedure.

The carbazole procedure involves measuring the amount of hexuronic acid (glucuronic acid) in the sample. A method for determining hexuronic acid concentration by a colorimetric method was reported by Dische et al. (1947) J. Biol. Chem., 167:189-198. The method is based on the color reaction of hexuronic acids with sulfuric acid and carbazole. An updated, automated method for the determination of hexuronic acids was reported by Balazs et al. (1965) Anal. Biochem., 12:547-558. The samples are heated in a sulfuric acid/borate medium and reacted with carbazole. The carbazole reacts with the hexuronic acid to form a pink complex with an absorbance maximum at 530 nm. For the automated method, the samples and standards are aspirated through a continuous flow analyzer using a peristaltic pump. The reagents (acid and carbazole) are added and heated in a reaction chamber, the absorbance is read by a continuous flow colorimeter at 530 nm.

Radioactivity content of the test article was determined by scintillation counting in an ISOCAP 300 liquid scintillation counter (Nuclear Chicago) using Scintiverse Bio HP (Fisher Scientific) as a scintillant. Raw CPM data was converted to DPM using the ISOCAP 300's external standards ratio program, with standardization against Tritium Liquid Scintillation Quench Standards, or Carbon-14 Liquid Scintillation Quench Standards (Amergham, Arlington Heights, Ill.).

F. Determination of Synvisc® (hylan G-F 20) Residence Half-Life

The clearance of Synvisc® (hylan G-F 20) and its gel and fluid components from the knee joint were determined in New Zealand White rabbits weighing between 2.5 and 3.5 kg. Rabbit were sacrificed at 24 hours, 3, 7, and 28 days, respectively. The radioactive material prepared essentially as described above was administered as an intra-articular injection of 0.3 ml (0.086 ml/kg body weight). This dose level is expected to be equivalent to a single 6 ml administration of Synvisc® (hylan G-F 20) to a 70 kg human. Corresponding amounts to be administered in other animals are likewise directly proportional to the weight of the animal.

DPMs were obtained for each tissue as outlined above, and DPM/mg was calculated directly when appropriate. The total DPMs recovered and both DPMs and DPM/mg for each joint tissue were calculated separately for each animal. These values were then averaged for each time point and, expressed as mean±the standard error of the mean. Calculated averages were reported to a minimum of two significant digits, even in situations where the values were small and the animal to animal variation was large. Total average DPM recovered from the joint at each time point was calculated by averaging the individual animal totals.

Half-life determinations were made by fitting the means for each time to an exponential function ($Y=Ae^{kx}$). The standard error of the estimate was obtained from the curve fit and divided by A to obtain the expected percent error. This was multiplied by the half-life to obtain the expected error of the half-life.

G. Results

The gel component (hylan B) of Synvisc® (hylan G-F 20) is the longer half-life moiety. Based on the clearance of the radioactive material, the gel component's residence half-life was determined to be 7.7-8.8 days. Thus, by day 30, more than 95% of the gel would be cleared. Theoretical calculations, based on the experimentally determined half-life of the gel, were conducted to estimate the amount of gel expected to be in the human joint following a single 6 ml injection. Assuming that approximately 6 mg of gel was injected into the knee of a human subject, at 21 days following the injection the amount of gel remaining would be approximately 0.9 mg.

The fluid component of Synvisc® (hylan G-F 20) (hylan A) clears more rapidly than the gel component. The half-life of the fluid component was determined to be 1.2-1.5 days. By 7 days, 99% of the injected material was cleared from the rabbit knee joint.

Rabbit muscle implant studies were also conducted. Microscopic examination at 7 and 30 days post-implantation did not detect any residual test material, which is consistent with the intra-articular clearance studies.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent the material incorporated by reference contradicts or is inconsistent with the present specification, the present specification will supersede any such material. The citation of any references herein is not an admission that such references are prior art to the present invention.

Unless otherwise indicated, all numbers expressing quantities of ingredients, cell culture and treatment conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

The invention claimed is:

1. A method for treating a knee joint of a subject suffering from osteoarthritis in said joint, the method comprising a treatment regimen, the regimen being characterized by the step of administering a single administration dose, within a 24 hour period, of a viscosupplement intra-articularly into the knee joint of said subject,
   wherein said viscosupplement administered in the single administration dose:
      is a hyaluronan (HA) based viscosupplement that does not contain additional active components, and
      comprises between 24 mg to 100 mg of HA, and
      comprises a crosslinked HA, and
      has a residence half-life in said knee joint of between 0.2 days to 8.8 days;
   wherein said treatment regimen does not comprise administering the viscosupplement in weekly intervals.

2. The method of claim 1, wherein the subject is human.

3. A method for treating a knee joint of a human subject suffering from a joint pathology, the method comprising a treatment regimen, the regimen being characterized by the step of administering a single administration dose, within a 24 hour period, of a viscosupplement intra-articularly into the knee joint of said human subject,
   wherein said viscosupplement administered in the single administration dose:
      is a hyaluronan (HA) based viscosupplement that does not contain additional active components, and
      comprises between 24 mg to 100 mg of HA, and
      comprises a crosslinked HA, and
      has a residence half-life in said knee joint of between 0.2 days to 8.8 days;
   wherein said treatment regimen does not comprise administering the viscosupplement in weekly intervals.

4. The method of claim 3, wherein the joint pathology is associated with osteoarthritis.

5. A method for treating osteoarthritic pain in a knee joint of a human subject, the method comprising a treatment regimen, the regimen being characterized by the step of administering a single administration dose, within a 24 hour period, of a viscosupplement intra-articularly into the knee joint of said human subject,
   wherein said viscosupplement administered in the single administration dose:
      is a hyaluronan (HA) based viscosupplement that does not contain additional active components, and
      comprises between 24 mg to 100 mg of HA, and
      comprises a crosslinked HA, and
      has a residence half-life in said knee joint of between 0.2 days to 8.8 days
   wherein said treatment regimen does not comprise administering the viscosupplement in weekly intervals.

6. The method of claim 1, 3 or 5, wherein the subject is in need of treatment of joint pain.

7. The method of claim 1, 3 or 5, wherein the viscosupplement comprises 8±2 mg/ml HA.

8. The method of claim 1, 3 or 5, wherein said HA is of animal origin.

9. The method of claim 8, wherein said HA is produced from rooster combs.

10. The method of claim 1, 3 or 5, wherein said HA is of bacterial origin.

11. The method of claim 1, 3 or 5, wherein said viscosupplement comprises HA crosslinked with formaldehyde.

12. The method of claim 11, wherein the average molecular weight of said HA crosslinked with formaldehyde is 6,000 kDa.

13. The method of claim 11, wherein at least part of said HA crosslinked with formaldehyde is present in a fluid form.

14. The method of claim 1, 3 or 5, wherein said viscosupplement comprises hylan A.

15. The method of claim 1, 3 or 5, wherein said viscosupplement comprises HA crosslinked with divinyl sulfone.

16. The method of claim 15, wherein said HA crosslinked with divinyl sulfone is present in a gel form.

17. The method of claim 1, 3 or 5, wherein said viscosupplement comprises hylan B.

18. The method of claim 1, 3 or 5, wherein the viscosupplement comprises hylan A and hylan B.

19. The method of claim 18, wherein the ratio of hylan A/hylan B is 9/1 by weight of HA.

20. The method of claim 18, wherein the single administration dose consists of a single injection of said viscosupplement.

21. The method of claim 1, 3 or 5, wherein the viscosupplement comprises 8±2 mg/ml of HA, wherein 10% of said HA by weight of HA is in a gel form.

22. The method of claim 1, 3 or 5, wherein the viscosupplement is hylan G-F 20.

23. The method of claim 22, wherein the single administration dose consists of a single injection of said viscosupplement.

24. The method of claim 1, 3 or 5, wherein 10% of said HA by weight of HA is in a gel form.

25. The method of claim 1, 3 or 5, wherein a therapeutic effect is assessed by:
   a) measuring an improvement in a degree of functional impairment of said knee joint;
   b) measuring a reduction in joint pain in said knee joint; or
   c) a global status assessment.

26. The method of claim 1, 3 or 5, wherein said viscosupplement comprises HA crosslinked with formaldehyde and divinyl sulfone.

27. The method of claim 26, wherein said HA crosslinked with formaldehyde and divinyl sulfone is present in a gel form.

28. A method for treating a knee joint of a human subject suffering from a joint pathology, the method comprising a treatment regimen, the regimen being characterized by the step of administering a single administration dose, within a 24 hour period, of 6 ml of a hyaluronan (HA) based viscosupplement that does not contain additional active components, intra-articularly into the knee joint of said human subject, wherein said treatment regimen does not comprise administering the viscosupplement in weekly intervals,
   wherein the HA based viscosupplement that does not contain additional active components is hylan G-F 20.

29. The method of claim 28, wherein the joint pathology is associated with osteoarthritis.

30. The method of claim 28, wherein said single administration dose consists of a single injection of said viscosupplement.

31. The method of claim 1, 3, 5 or 28, wherein said single administration dose consists of a single injection or multiple injections of said viscosupplement.

32. The method of claim 1, 3, 5 or 28, wherein said single administration dose consists of a single injection of said viscosupplement.

* * * * *